United States Patent [19]
Sullivan et al.

[11] Patent Number: 5,598,888
[45] Date of Patent: Feb. 4, 1997

[54] CRYOGENIC TEMPERATURE GRADIENT MICROSCOPY CHAMBER

[75] Inventors: Edward V. Sullivan, Huntington Station; Louis G. Casagrande, Malverne; Fred Edelstein, Hauppauge; John M. Papazian, Great Neck, all of N.Y.

[73] Assignee: Grumman Aerospace Corporation, Los Angeles, Calif.

[21] Appl. No.: 311,429

[22] Filed: Sep. 23, 1994

[51] Int. Cl.$^6$ .................................................. F25B 29/00
[52] U.S. Cl. ........................................ 165/263; 359/395
[58] Field of Search ............................. 359/395, 398; 165/30

[56] References Cited

U.S. PATENT DOCUMENTS

| | | | |
|---|---|---|---|
| 2,232,354 | 2/1941 | Weygand | 359/395 |
| 3,230,773 | 1/1966 | Matthews | 359/395 |
| 4,629,862 | 12/1986 | Kitagawa et al. | 359/395 |
| 4,707,086 | 11/1987 | Dahan et al. | 359/398 |
| 4,984,628 | 1/1991 | Uchida et al. | 165/30 |
| 5,181,382 | 1/1993 | Middlebrock | 359/398 |
| 5,257,128 | 10/1993 | Diller et al. | 359/398 |
| 5,410,429 | 4/1995 | Focht | 359/398 |

*Primary Examiner*—F. Daniel Lopez
*Assistant Examiner*—Mark Sgantzos
*Attorney, Agent, or Firm*—Terry J. Anderson; Karl J. Hoch, Jr.

[57] ABSTRACT

A controlled low temperature chamber for a microscope has a vacuum chamber in a housing. The housing has a top panel and a bottom panel. A mounting in the chamber mounts a sample in a manner whereby the sample is microscopically observable. The mounting includes a base member, a pair of spaced supports extending perpendicularly from the base member and a pair of spaced platforms supported by the supports. Each of the platforms has an upper surface on which the sample rests and a spaced undersurface beneath the sample. A temperature control system maintains a specified temperature in the chamber, applies a controlled temperature gradient on the sample and moves the gradient along the sample in a controlled manner, thereby directionally solidifying and melting the sample, as desired.

19 Claims, 4 Drawing Sheets

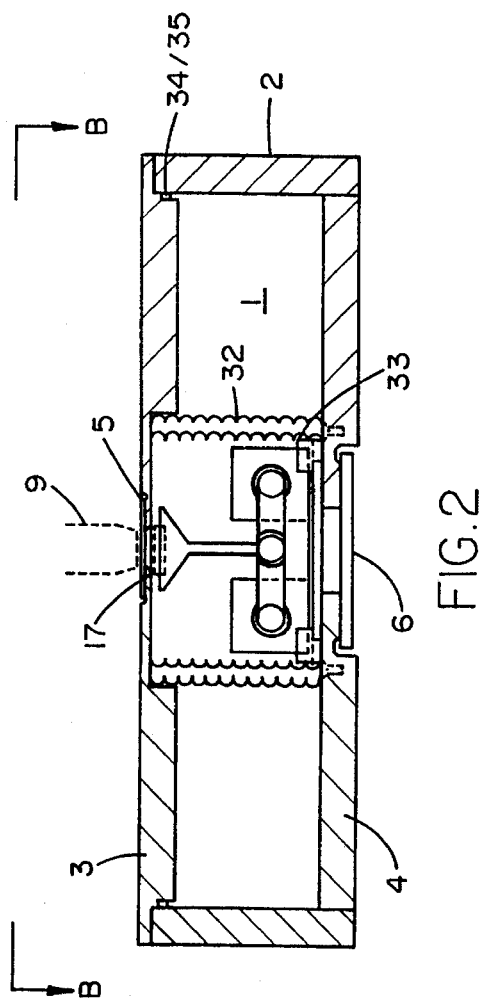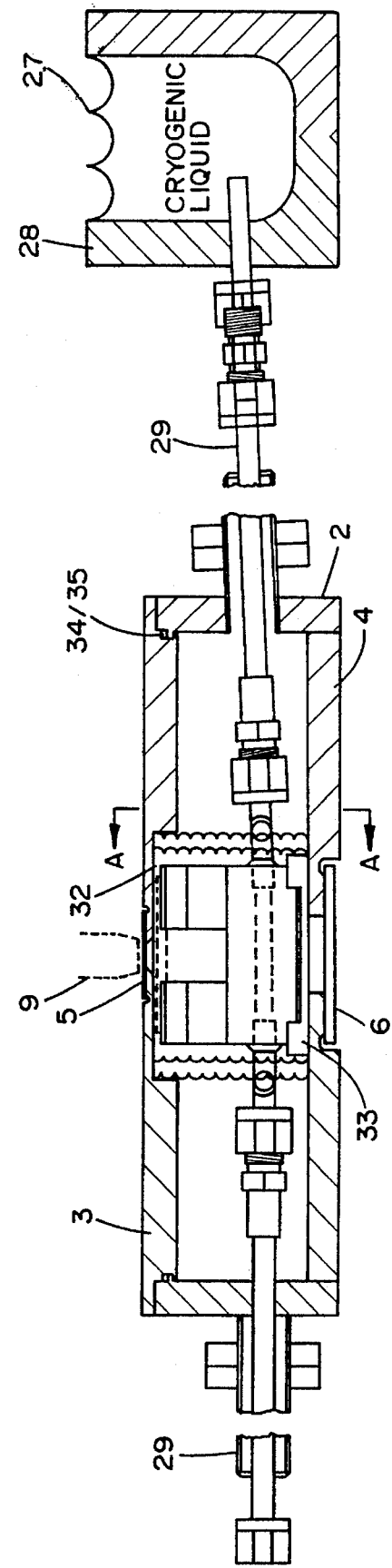

CRYOGENIC TEMPERATURE GRADIENT MICROSCOPY CHAMBER

BACKGROUND OF THE INVENTION

Field of the Invention

The present invention relates to a controlled low temperature chamber for a microscope.

It is necessary in many phases of technological development to observe materials at very low temperatures in the cryogenic range. Such observation permits study of the melting and solidification characteristics of materials with low melting points as well as other aspects of the behavior of materials at low temperatures.

The principal object of the invention is to provide an apparatus for permitting microscopic observation of materials in a low temperature environment.

An object of the invention is to provide an apparatus which permits the observation of materials with an optical microscope at controlled, variable, low temperatures, down to 4 degrees K.

Another object of the invention is to provide an apparatus which permits study of the melting and solidification characteristics of materials with low melting points as well as other aspects of the behavior of materials at low temperatures.

Still another object of the invention is to provide an apparatus which is capable of imposing a controlled or zero temperature gradient on a sample and of moving such gradient along such sample in a controlled manner, thereby directionally solidifying or melting such sample.

Yet another object of the invention is to provide a controlled low temperature chamber for a microscope.

Another object of the invention is to provide a controlled low temperature chamber for a microscope which chamber is mountable on a standard microscope stage, whereby a sample in such chamber may be scanned by motion of such stage and the progress of solidification or melting reactions may be monitored in situ.

BRIEF SUMMARY OF THE INVENTION

In accordance with the invention, a controlled low temperature chamber for a microscope comprises a vacuum chamber in a housing having a top surface, a bottom surface, and a cylindrical chamber. A mounting in the chamber mounts a sample in a manner whereby the sample is microscopically observable. A temperature control system maintains a cryogenic temperature in the chamber, applies a controlled temperature gradient on the sample and moves the gradient along the sample in a controlled manner, thereby directionally solidifying or melting the sample, as desired.

Part of the top and bottom surfaces of the chamber housing are transparent. The transparent part of the top surface consists of a substantially clear window viewing port, which may be sapphire, and the transparent part of the bottom surface consists of a substantially clear window, which may be glass.

The mounting includes a pair of spaced platforms each having an upper surface on which the sample rests and an undersurface. The temperature control system includes independent electric heaters on the undersurfaces of the platforms, thermal sensors of any suitable known type positioned along the sample, and a computer controlling the energization of the electric heaters, thereby permitting independent stabilization of each end of the sample to any selected temperature. A selected temperature gradient is imposed across the sample, and the electric heaters modify the gradient or move it along the sample as desired. The temperature control system further includes a system for circulating a temperature control fluid, such as, liquid nitrogen, ethylene glycol, water, or hot oil in the mounting. The combination of temperature control fluid and electric heaters permit melting and solidification reactions in a sample to be observed via the top surface of the chamber housing via light transmitted through the bottom surface of the chamber housing or reflected through the top surface.

The chamber housing is of substantially cylindrical configuration and consists of a thermally insulating material, such as, for example, stainless steel, and the platforms of the mounting consist of thermally conductive material, such as, for example, aluminum. The mounting further includes a pair of isolated supports supporting the platforms and a base member on which the supports are mounted and from which the supports extend substantially perpendicularly. The chamber housing is of cylindrical configuration. The top and bottom surfaces are substantially planar and the top surface is removably coupled to the housing in a fluid-tight manner.

The liquid nitrogen system circulates liquid nitrogen through the base member of the mounting. Multilayer insulation in the chamber surrounds the mounting for insulating the platforms of the mounting from the warm temperature of the chamber housing.

In accordance with the invention, a controlled low temperature chamber for a microscope comprises a vacuum chamber in a housing having a top panel and a bottom panel. A mounting in the chamber mounts a sample in a manner whereby the sample is microscopically observable. The mounting includes a base member, a pair of spaced supports extending substantially perpendicularly from the base member and a pair of spaced platforms supported by the supports. Each of the platforms has an upper surface on which the sample rests and a spaced undersurface beneath the sample. A vessel supported by, and extending between, the upper surfaces of the pair of platforms accommodates the sample. A temperature control system maintains a cryogenic temperature in the chamber, applies a controlled temperature gradient on the sample, and moves the gradient along the sample in a controlled manner, thereby directionally solidifying or melting the sample, as desired. The temperature control system includes independent electric heaters on the undersurfaces of the platforms, thermal sensors of any suitable known type positioned along the sample, and a computer controlling the energization of the electric heaters, thereby permitting independent stabilization of each end of the sample to any selected temperature. A selected temperature gradient is imposed across the sample and the electric heaters modify the gradient and move it along the sample as desired. A temperature control system circulates the temperature control fluid in the mounting, whereby the combination of the temperature control fluid and electric heaters permits melting and solidification reactions in a sample to be observed via the top panel of the chamber housing. The temperature control system circulates a temperature control fluid through the base member of the mounting.

The supports of the mounting provide a limited, known heat transfer between the platforms and the base. The supports of the mounting are substantially coplanar and perpendicular to the base and the platforms of the mounting are substantially coplanar, substantially parallel to the base member and spaced from the base member. The mounting consists of any suitable thermal conductor, such as, for example, aluminum. The geometry and materials of the mounting are selected to provide the desired thermal environment.

The chamber housing consists of a stainless steel cylinder. The top panel of the chamber housing has a transparent window therein and the bottom panel of the chamber housing has a transparent window therein. The window in the top panel of the chamber housing is substantially clear and may be sapphire, and the window in the bottom panel of the chamber housing is substantially clear and may be glass. Multilayer insulation in the chamber surrounding the mounting insulates the platforms of the mounting from the warm temperatures of the chamber housing. The top and bottom panels of the chamber housing are substantially planar and the top panel is removably coupled to the housing in a fluid-tight manner.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

In the drawings, wherein similar reference characters denote similar elements throughout the several views:

FIG. 1 is a side view, partly in section and partly cut away, of an embodiment of the controlled low temperature chamber of the invention;

FIG. 2 is a sectional view, taken along the line A—A of FIG. 1;

DETAILED DESCRIPTION OF PREFERRED EMBODIMENTS

Although the controlled temperature chamber of the invention is described as an essentially cryogenic chamber, the chamber may function at non-cryogenic temperatures and maintains the dual-temperature aspect for imposition of a temperature gradient. Thus, any temperature below the melting point of the mounting, for which there is a suitable control fluid, may be a suitable chamber temperature.

Figure 3:
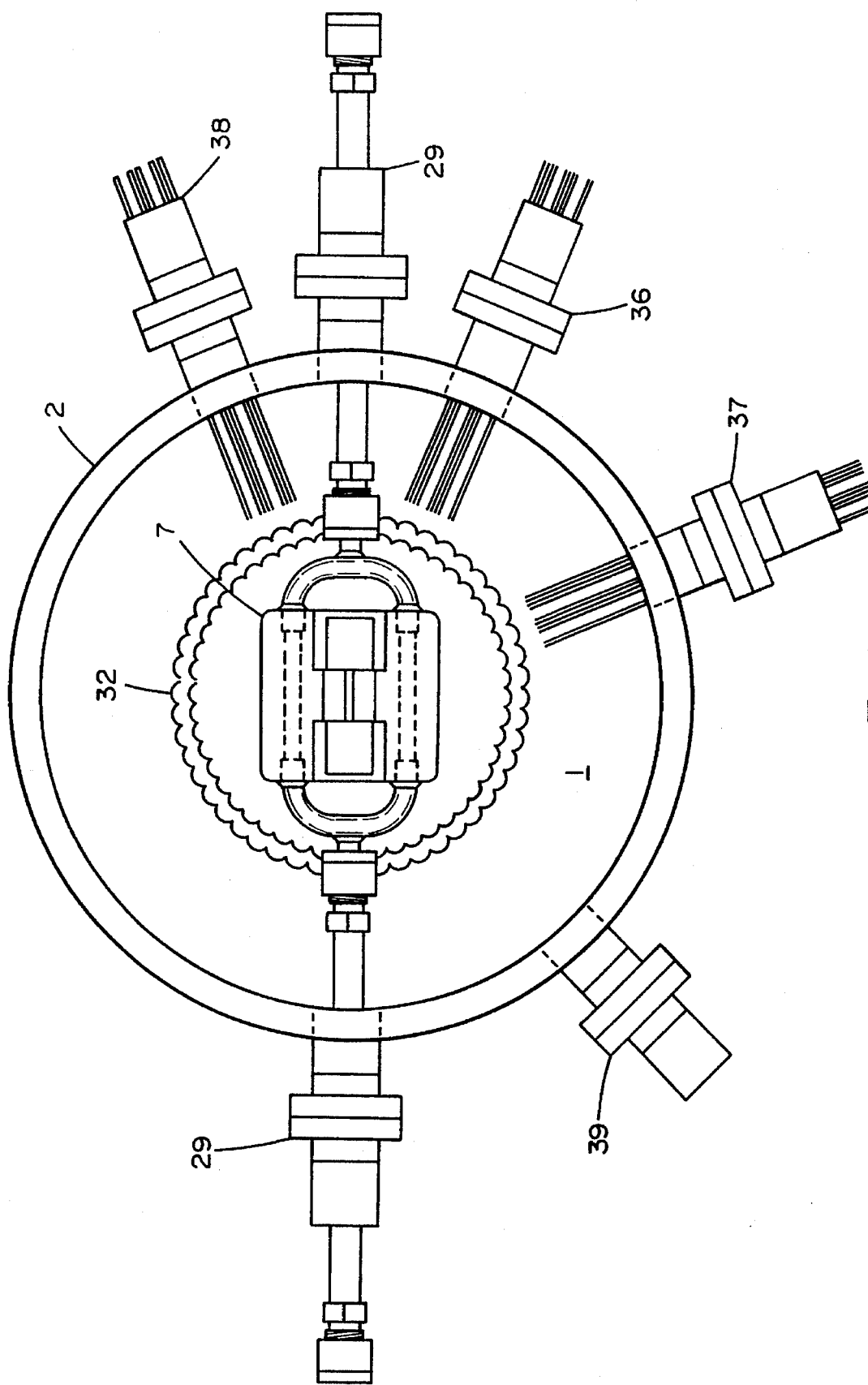
FIG. 3 is a top or axial view, taken along the line B—B of FIG. 3, with the top panel off.

Turning now in detail to the drawings, the controlled low temperature chamber of the invention, shown in the Figures, is for a microscope and comprises a vacuum chamber 1 in a housing 2 (FIGS. 1 and 2) having a top panel 3 and a bottom panel 4 (FIGS. 1 and 2). The chamber housing 2 preferably consists of a stainless steel cylinder, as shown in FIGS. 1 to 3. The top panel 3 of housing 2 has a transparent window 5 therein, of very thin hemex grade sapphire. Window 5 functions as a viewing port which allows for a short focal length, while maintaining the strength required for vacuum. Viewing port 5 has a thickness of 0.016 inch and a diameter of 1.0 inch. Bottom panel 4 has a transparent window 6 therein of optically clear glass. Both windows 5 and 6 are seated and sealed in place with a compatible vacuum-low temperature sealing compound of any suitable known type. The top and bottom panels 3 and 4, respectively, are substantially planar. Top panel 3 is removably coupled to housing 2 in a pressure-fitted or fluid-tight manner. Bottom panel 4 is stationary.

The chamber housing 2 has feedthroughs for a temperature control system, power for an electric heating system, temperature or thermal sensors and a vacuum port.

Figure 4:
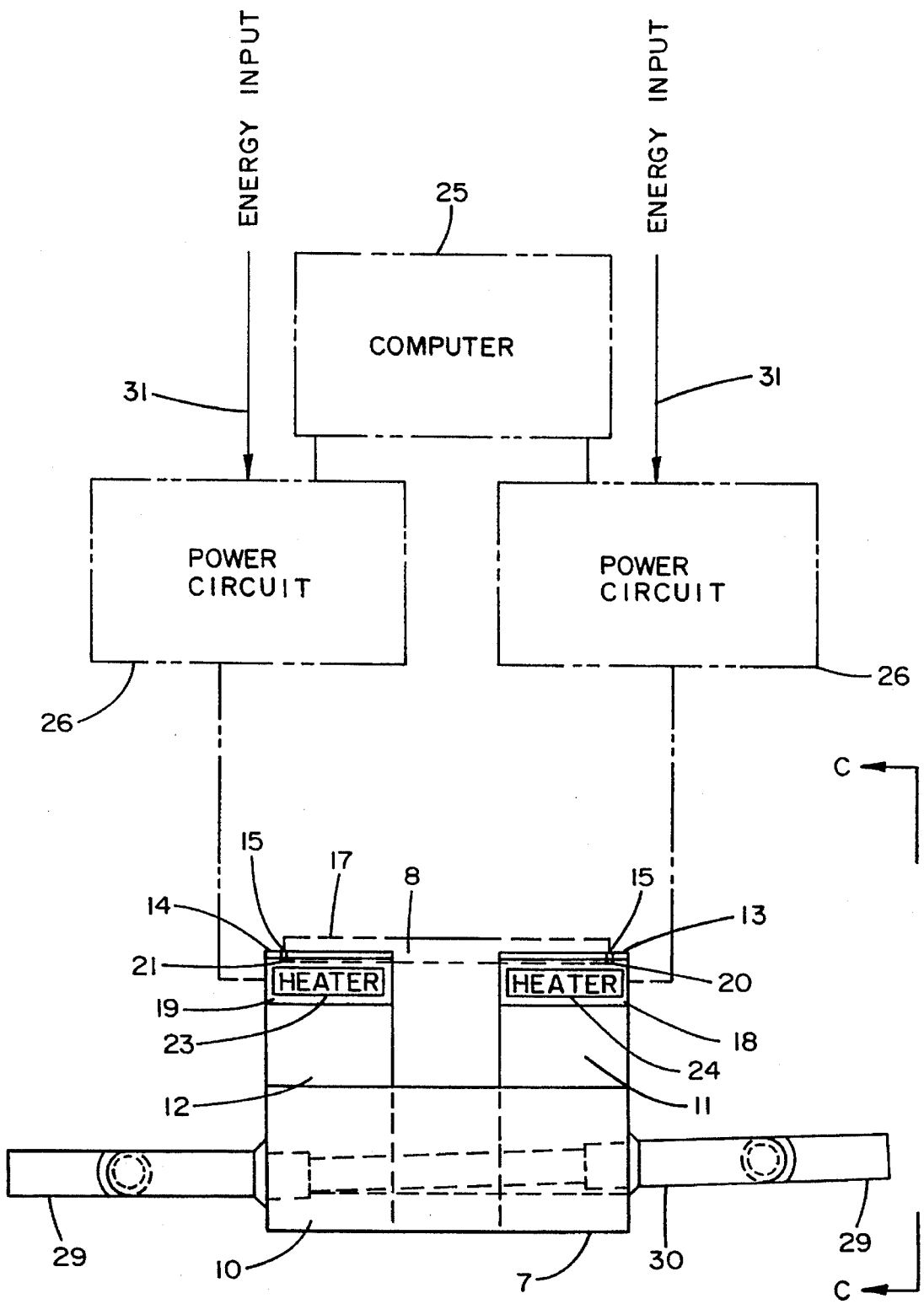
FIG. 4 is a side view, full size, of the mounting of the embodiment of FIGS. 1 to 3.
Figure 5:
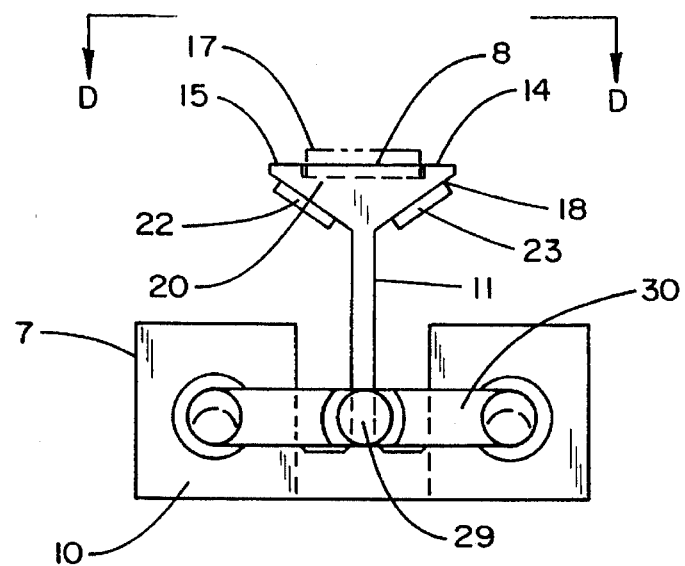
FIG. 5 is a view, taken along line C—C of FIG. 4.
Figure 6:
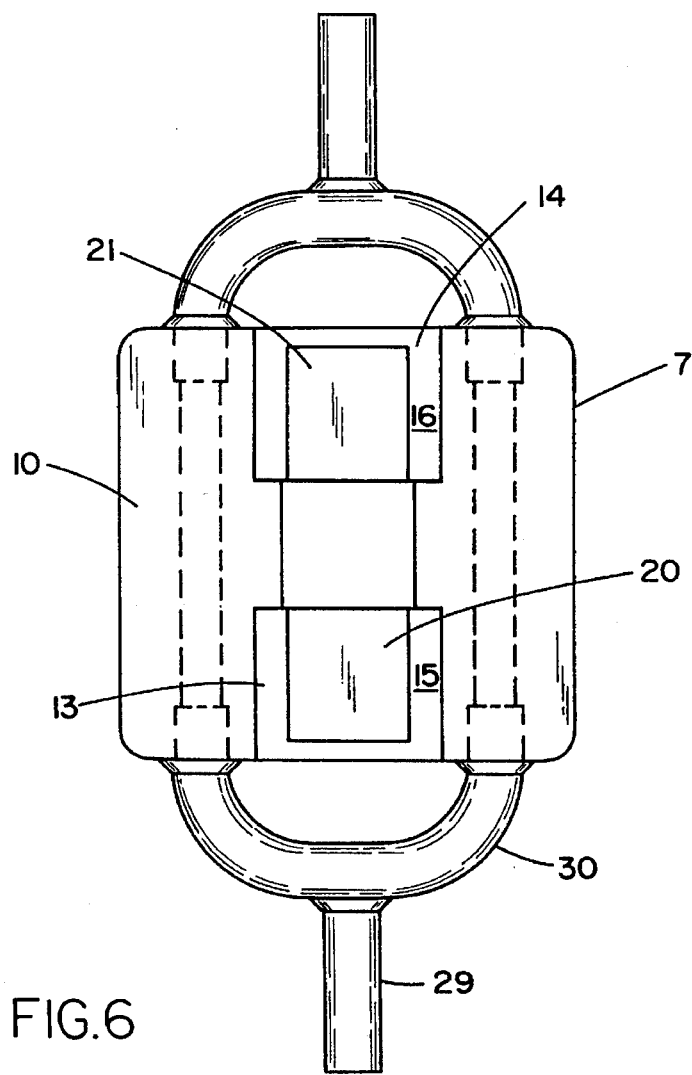
FIG. 6 is a view, taken along the lines D—D of FIG. 5.

A mounting 7 (FIGS. 3 to 6) in the chamber 1 mounts a sample 8 (FIGS. 4 and 5) in a manner whereby said sample is microscopically observable via a microscope, part 9 of which, for example, is shown in FIGS. 1 and 2. The mounting 7 has a base member 10 (FIGS. 4 to 6) and a pair of spaced supports 11 and 12 extending perpendicularly from the base member 10 (FIGS. 4, 5 and 6). Supports 11 and 12 are substantially coplanar, as shown in FIGS. 4 and 5. A pair of spaced platforms 13 and 14 (FIGS. 4 and 6) are supported by the supports 11 and 12, respectively. Platforms 13 and 14 of the mounting are substantially coplanar, substantially parallel to base member 10 and spaced from said base member. The mounting consists of aluminum to maximize thermal conductivity while maintaining facility of initial machining.

The cylindrical housing 2 being of stainless steel reduces condensation on windows 5 and 6 and provides a thermal barrier for aluminum mounting 7. Window 6 is used as a light source path to microscope lens 9 through the mounting 7 from the microscope light supply. Platforms 13 and 14 have upper surfaces 15 and 16, respectively (FIGS. 4 to 6), which support a cuvette, or laboratory experimentation vessel, 17 of any suitable known type (FIGS. 1, 2, 4 and 5). The vessel 17 accommodates sample 8 (FIGS. 4 and 5). The platforms 13 and 14 have separate undersurfaces 18 and 19, respectively, beneath sample 8 (FIG. 4). In order to retain vessel 17 motionless, upper surfaces 15 and 16 of platforms 13 and 14, respectively, have recesses 20 and 21, respectively, formed therein.

A temperature control system maintains a cryogenic temperature in chamber 1 and applies a controlled temperature gradient on sample 8. The temperature control system also moves the gradient along sample 8 in a controlled manner, thereby directionally solidifying or melting said sample, as desired. The temperature control system includes electric heaters 22 and 23 (FIGS. 4 and 5) on undersurfaces 18 of platform 13 and an electric heater 24 (FIG. 4) on undersurface 19 of platform 14 and another electric heater (not shown in the FIGS.) on said undersurface 19. Thermal or temperature sensors 40 to 47 of any suitable known type are positioned on platforms 13 and 14 and spaced along the observation area (FIG. 6).

A computer 25, of any suitable known type, receives temperature data from the thermal sensors on platforms 13 and 14 and controls the energization of electric heaters 22, 23, 24 and so on, via an electrical power circuit 26 of any suitable known type. This permits independent stabilization of each end of sample 8 to any selected temperature, whereby a selected temperature gradient is imposed across said sample and the electric heaters to modify the gradient and move it up or down, as desired.

The temperature control system also includes a coolant system for circulating any suitable coolant, such as, for example, liquid nitrogen, or any suitable control fluid in mounting 7. The combination of control fluid cooling and electrical heating permits melting and solidification reactions in a sample to be observed via viewing port 5 of top panel 3 of chamber housing 2 via light transmitted through the bottom window 6 of said housing or light reflected from above through top window 5 of said housing. The liquid nitrogen system has a liquid nitrogen supply 27 in a storage facility 28 for liquid nitrogen (FIG. 1). Liquid nitrogen 27 is supplied from storage facility 28 via input tubes 29 (FIGS. 1 and 3 to 6) to base member 10 of mounting 7 via a "Y" connector 30 (FIGS. 3 to 6).

The liquid nitrogen system circulates liquid nitrogen through base member 10 of mounting 7. The liquid nitrogen is distributed equally to both halves of base member 10. Platforms 13 and 14 are cooled by conduction through their supports 11 and 12, respectively, which are in contact with the liquid nitrogen heat sink in both halves of base member 10. This results in the cooling of vessel 17, which is restrained by recesses 20 and 21. The electric heaters 22, 23, 24, and so on, as hereinbefore described, provide a controlled temperature environment to vessel 17. The electric energy is supplied to chamber 1 via an energy input feed through line 31 (FIGS. 3 and 4).

The chamber 1 is a custom configured container which permits specific tests to be undertaken in a controlled temperature and vacuum environment. The computer 25 and power circuit 26 connected to electric heaters 22, 23, 24, and so on, permit independent stabilization of each end of sample 8 to any selected temperature. Thus, a selected temperature gradient may be imposed across sample 8 and the computer control system can modify such gradient, or move it along said sample in any desired fashion. The spacing of supports 11 and 12 from each other and window 6 in bottom panel 4 permit melting and solidification reactions in transparent samples to be observed by means of light transmitted from beneath housing 2. The apparatus of the invention may be used, however, for any optical observations at low temperatures.

The sample 8 need not be transparent. Observations may be made with reflected light supplied through the lens of microscope 9, as is common practice in metallurgical applications. The chamber 1 may also be used to study isothermal phenomena by maintaining the same temperature at each of supports 11 and 12, and making temperature changes in parallel. In this manner, the equiaxed, or casting, solidification behavior of materials at low temperatures may be observed. The temperature environment can be controlled, via computer 25 and power circuit 26, and a gradient applied across vessel 17 and varied with time, so that crystallization may be viewed as the liquid solid interface moves along said vessel.

The mounting 7 is insulated from the warm housing 2 by multilayer insulation (MLI) 32 (FIGS. 1 to 3) of any suitable known type, in chamber 1 surrounding said mounting. A block insulating material 33 (FIGS. 1 and 2) of any suitable known type such as, for example, fiberglass G-10, functions as a thermal barrier for base member 10 and provides a determined height for vessel 17, thereby minimizing the focal path length.

The lesser outer diameter of top panel 3 has an O-ring groove 34 formed therein (FIG. 3). An O-ring 35 (FIGS. 1 to 3) is placed in O-ring groove 34 (FIG. 3) and maintains a vacuum seal between housing 2 and the top panel 3 (FIG. 2). Housing 2 has three electrical feedthroughs 36, 37 and 38 (FIG. 3) with removable vacuum seals and flanges for facility of disassembly, maintenance and/or repair. The feedthroughs 36 and 37 are thermocouple feedthroughs. Housing 2 also has a vacuum port feedthrough 39 (FIG. 3).

While a single embodiment of the present invention has been shown and described, it is to be understood that many changes and modifications may be made thereunto without departing from the spirit and scope of the invention as defined in the appended claims.

What is claimed is:

1. A controlled low temperature chamber for a microscope, comprising:

a housing forming a vacuum chamber having a top surface and a bottom surface;

mounting means in said chamber for mounting a sample therein for microscopic observation; and a temperature control system for maintaining a cryogenic temperature in the chamber for applying a temperature gradient along said sample and for moving, and controlling movement of the temperature gradient along said sample to directionally solidify and melt said sample.

2. A controlled low temperature chamber for a microscope as claimed in claim 1, wherein part of the top surface and part of the bottom surface of said housing are substantially transparent.

3. A controlled low temperature chamber for a microscope as claimed in claim 2, wherein the part of said top surface consists of a viewing port and the part of said bottom surface consists of a substantially clear window.

4. A controlled low temperature chamber for a microscope as claimed in claim 2, wherein said mounting means includes a pair of spaced platforms each having an upper surface on which said sample rests and an undersurface, and said temperature control system includes independent electric heating means on said undersurfaces of the platforms and thermal sensors positioned along the sample and computer means controlling the energization of said electric heating means, thereby permitting independent stabilization of each end of the sample to any selected temperature, whereby a selected temperature gradient is imposed across said sample and said electric heating means modifies the gradient and moves said gradient along said sample.

5. A controlled low temperature chamber for a microscope as claimed in claim 4, wherein said temperature control system further includes means for circulating a temperature control fluid in said mounting means, whereby the combination of the temperature control fluid and electric heating means permits melting and solidification reactions in the sample to be observed through said top surface of said chamber housing via one of light transmitted through said bottom surface of said chamber housing and light reflected through said top surface of said housing.

6. A controlled low temperature chamber for a microscope as claimed in claim 5, wherein said temperature control fluid consists of one of the group consisting of liquid nitrogen, ethylene glycol, water and hot oil.

7. A controlled low temperature chamber for a microscope as claimed in claim 4, wherein said chamber housing is of substantially cylindrical configuration and consists of stainless steel and said platforms of said mounting means consist of thermally conductive material.

8. A controlled low temperature chamber for a microscope, as claimed in claim 4, further comprising a vessel supported by and extending between the upper surfaces of said pair of platforms for accommodating said sample.

9. A controlled low temperature chamber for a microscope as claimed in claim 5, wherein said mounting means further includes a pair of isolated supports supporting said platforms and a base member on which said supports are mounted and from which said supports extend substantially perpendicularly.

10. A controlled low temperature chamber for a microscope as claimed in claim 7, wherein said housing further includes a cylindrical sidewall, said top and bottom surfaces are substantially planar, said top surface is removably coupled to said sidewall, and said sidewall and said upper surface form a fluid-tight seal therebetween.

11. A controlled low temperature chamber for a microscope as claimed in claim 9, wherein said temperature control system circulates said temperature control fluid through the base member of said mounting means.

12. A controlled low temperature chamber for a microscope as claimed in claim 11, further comprising multilayer insulation in said chamber and surrounding said mounting means for insulating said platforms of said mounting means from warm temperature of said chamber housing.

13. A controlled low temperature chamber for a microscope comprising:

a housing forming a vacuum chamber and having a top panel and a bottom panel;

mounting means in said chamber for mounting a sample therein for microscopic observation, said mounting means including a base member, a pair of spaced supports extending substantially perpendicularly from the base member and a pair of spaced platforms supported by said supports, each of the platforms having an upper surface to support said sample and a spaced undersurface beneath said upper surface; and a temperature control system for maintaining a cryogenic temperature in the chamber, for applying a controlled temperature gradient on said sample and for moving, and controlling movement of, the temperature gradient along said sample to directionally solidify and melt said sample, said temperature control system including
  i) independent electric heating means on said undersurfaces of said platforms,
  ii) thermal sensors positioned along said sample,
  iii) computer means controlling the energization of said electric heating means, thereby permitting independent stabilization of each end of the sample to any selected temperature, whereby a selected temperature gradient is imposed across said sample and said electric heating means modified the gradient and moves the gradient along said sample, and
  iv) temperature control means for circulating a temperature control fluid in said mounting means, whereby the combination of the temperature control fluid and electric heating means permits melting and solidification reactions in the sample to be observed via said top panel of said chamber housing via one of light transmitted through said bottom surface of said chamber housing, and light reflected through the top surface of said chamber housing said temperature control means circulating the temperature control fluid through the base member of said mounting means.

14. A controlled low temperature chamber for a microscope as claimed in claim 13, wherein said supports of said mounting means are substantially coplanar and said platforms of said mounting means are substantially coplanar, substantially parallel to said base member and spaced from said base member.

15. A controlled low temperature chamber for a microscope as claimed in claim 13, wherein said chamber housing includes a stainless steel cylinder, the top panel of said chamber housing has a transparent window therein and the bottom panel of said chamber housing has a transparent window therein.

16. A controlled low temperature chamber for a microscope as claimed in claim 13, further comprising a vessel supported by and extending between the upper surfaces of said pair of platforms for accommodating said sample.

17. A controlled low temperature chamber for a microscope as claimed in claim 13, wherein said platforms of said mounting means consist of thermally conductive material.

18. A controlled low temperature chamber for a microscope as claimed in claim 15, wherein the window in said top panel of said chamber housing is sapphire and the window in said bottom panel of said chamber housing is substantially clear glass.

19. A controlled low temperature chamber as claimed in claim 15, further comprising multilayer insulation in said chamber and surrounding said mounting means for insulating said platforms of said mounting means from warm temperature of said chamber housing, and wherein said top and bottom panels of said chamber housing are substantially planar, said top panel is removably coupled to said cylinder, and said cylinder and said top panel form a fluid-tight seal therebetween.

* * * * *